(12) United States Patent
Andreini et al.

(10) Patent No.: US 6,623,499 B1
(45) Date of Patent: Sep. 23, 2003

(54) RETRACTABLE SAFETY SCALPEL

(76) Inventors: Michael Andreini, 1280 McDougal Green, Stillwater, MN (US) 55082; Dan Titcomb, 761 Goodrich Ave., St Paul, MN (US) 55105

( * ) Notice: Subject to any disclaimer, the term of this patent is extended or adjusted under 35 U.S.C. 154(b) by 0 days.

(21) Appl. No.: 10/081,570

(22) Filed: Feb. 21, 2002

(51) Int. Cl.[7] .............................................. A61B 17/32
(52) U.S. Cl. ........................ 606/167; 30/335; 30/329
(58) Field of Search ................... 606/167, 168, 606/170, 172; 30/329, 335

(56) References Cited

U.S. PATENT DOCUMENTS

| | | | | | |
|---|---|---|---|---|---|
| 5,139,507 | A | * | 8/1992 | Dolgin et al. | 606/167 |
| 5,207,696 | A | * | 5/1993 | Matwijcow | 606/167 |
| 5,403,337 | A | * | 4/1995 | Platts | 606/167 |
| 5,431,672 | A | * | 7/1995 | Cote et al. | 606/167 |
| 5,620,454 | A | * | 4/1997 | Pierce et al. | 606/167 |
| 5,730,751 | A | * | 3/1998 | Dillon et al. | 606/167 |
| 5,776,156 | A | * | 7/1998 | Shikhman | 606/170 |
| 5,908,432 | A | * | 6/1999 | Pan | 606/167 |
| 6,022,364 | A | * | 2/2000 | Flumene et al. | 606/166 |
| 6,254,621 | B1 | * | 7/2001 | Shackelford et al. | 606/167 |
| 6,267,759 | B1 | * | 7/2001 | Quick | 606/47 |

* cited by examiner

*Primary Examiner*—Michael J. Milano
*Assistant Examiner*—Charles H. Sam
(74) *Attorney, Agent, or Firm*—Beck & Tysver, P.L.L.C.

(57) ABSTRACT

The present invention is a scalpel with a retractable blade which may be advanced or retracted by operation of a slider. The scalpel has multiple operating positions and the physician may conveniently retract the blade by actuating the slider.

7 Claims, 2 Drawing Sheets

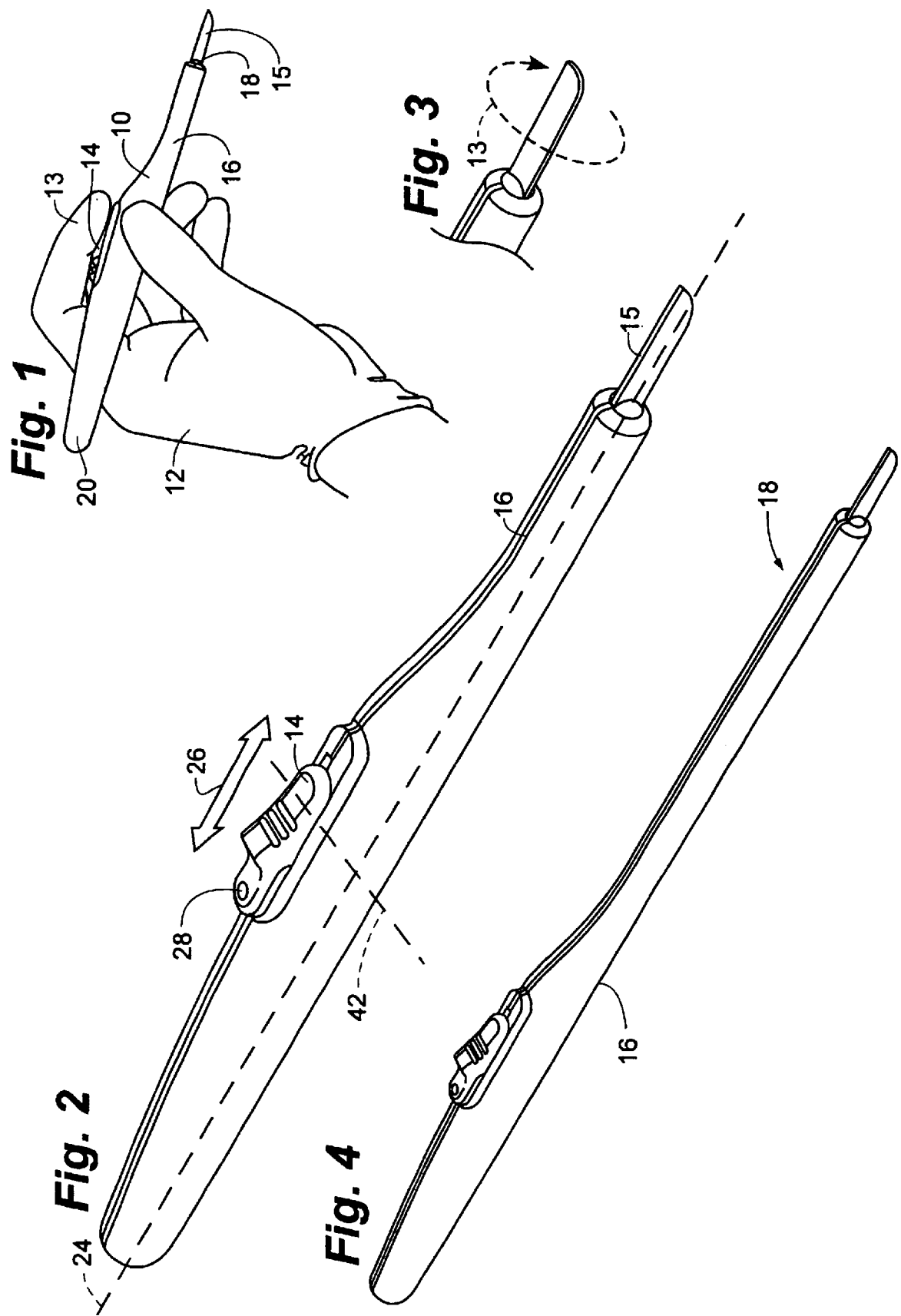

RETRACTABLE SAFETY SCALPEL

FIELD OF INVENTION

The present invention relates generally to the field of surgical instruments and more particularly to a scalpel type cutting instrument which is designed to be manipulated by the hand of a physician.

BACKGROUND OF THE INVENTION

Surgical cutting instruments such as scalpels are widely used to perform surgery. A variety of blade configurations are widely available. The traditional scalpel consists of a blade fixed to a handle. In operation the handle is manipulated by the physician to make an incision. Although infrequent the exposed cutting surface of the traditional scalpel can inadvertently cut the physician or surgical assistant. The potential for blood born infection has created a demand for surgical instruments which retract or otherwise shield the user from inadvertent "pricks". For example a wide variety of scalpels with retractable blades are available in the industry. See for example U.S. Pat. No. 5,403,337. Although "safe" surgical instruments are now widely available there is a continuing need to improve the performance of such devices so that they meet the users' expectations in terms of performance as a surgical instrument as well as offer improved safety.

SUMMARY OF INVENTION

In contrast to prior art devices the present cutting tool incorporates a number of features. In one embodiment the blade may be rotated about its major axis providing a variety of cutting angles for a given handle position. In another embodiment the blade orientation is fixed.

In all embodiments the blade retracts into the handle which defines the closed position. The blade is biased toward a closed configuration by a spring feature which may be activated by a finger release. When the finger release is activated the blade is automatically retracted into the body of the device. To move the blade into the "open" or operating position the user moves the finger slider toward the proximal end of the handle and a combination of gears and racks advances the blade out of the distal tip of the body.

BRIEF DESCRIPTION OF DRAWINGS

Throughout the several figures of the drawings identical reference numerals refer to identical structure throughout. An exemplary form of the device is shown in the figure and numerous departures may be made without departing from the scope of the invention wherein;

FIG. 1 is a respective view of the device in use;

FIG. 2 is a perspective view of the device with the blade in the "open" operating position;

FIG. 3 is figure showing a partial view of a portion of the scalpel;

FIG. 4 is a perspective view of a laparoscopic version of the device;

DETAILED DESCRIPTION

Figure 5:
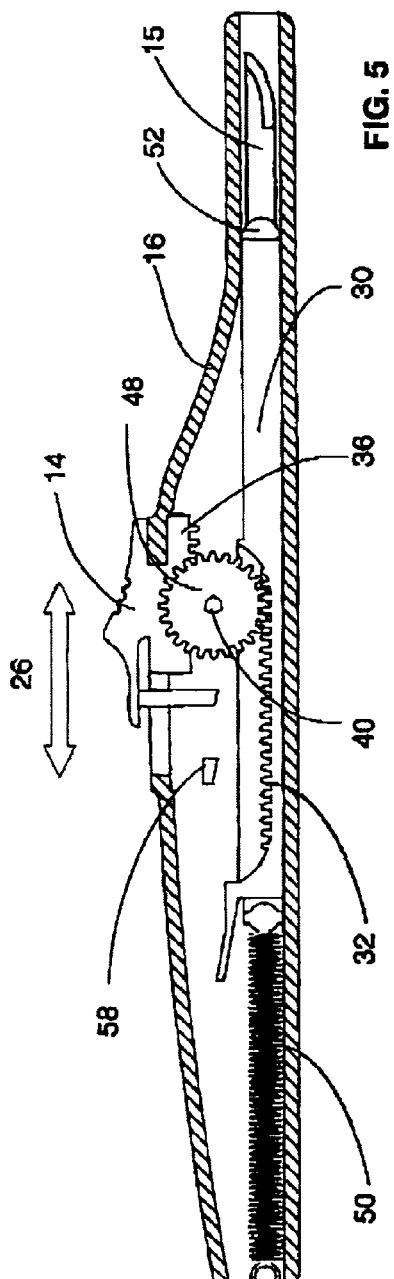
FIG. 5 is a cross-section of the device is a figure with the blade in a retracted "closed" position.

In FIG. 1 the surgical tool or device 10 is being held in a users hand 12. The index finger 13 is on the finger slider 14 which is used to advance the blade 15 out of the body 16. The blade emerges from the distal end 18 of the body 16 and the body 16 forms a handle that rests comfortably in the hand of the user with the proximal end 20 of the body 16 cradled in the "crook" of the hand.

FIG. 4 shows an extended version of the device for use in a laparoscopic surgical procedure. The nose 15 of the body member is extended for a length of several inches and the outer surface is round to make the tool compatible with surgical ports. It is anticipated that the interior portion of the body member will be sealed with an o-ring or the like to prevent gas from passing through the instrument.

FIG. 2 is a perspective view of the device in isolation. It shows the axis 24 which extends the length of the body 16. The figure shows the slider 14 which may be advanced or retracted along the path 26 which is preferably parallel to the axis 24. The finger slider carries at its rear most portion a blade release 28 which may be conveniently operated by the index finger when actuation is intended.

It is preferred to incorporate the blade release 28 into the moveable finger slider 14. The blade release 28 may be used to release the blade from a locked condition. The blade may retract quickly and automatically if the index finger is removed from the slider or the user's finger may be used to control the retraction of the blade into the body. In the preferred embodiment the blade is biased into the retracted position, although unbiased versions may be preferred by some users.

FIG. 3 is a partial view of the distal end of the device showing an embodiment where the blade may be rotated as depicted by arrow 13 around the central axis. Some physicians prefer the ability to cut at an angle.

Figure 6:
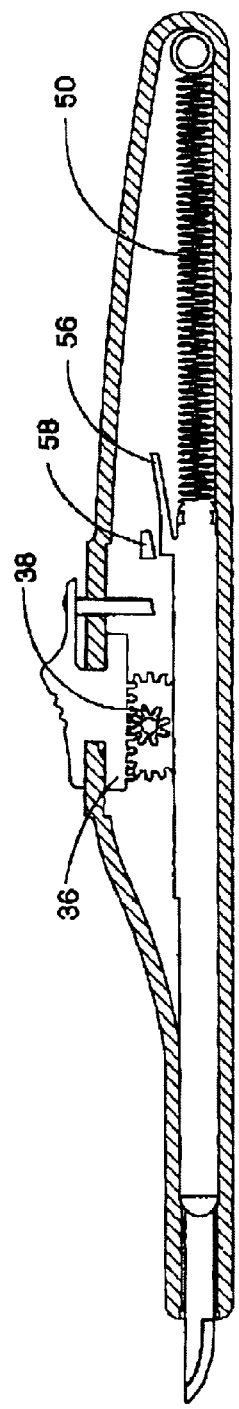
FIG. 6 is a cross-section of the device with the blade in an intermediate position; and, FIG. 7 is a cross-section of the device with the blade in the fully advanced or "open" position.
Figure 7:
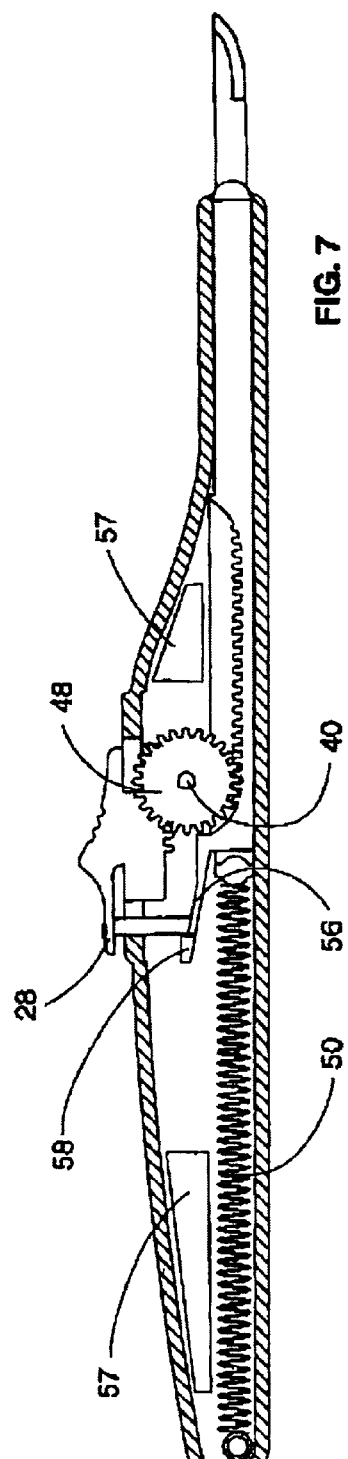

FIGS. 5, 6, and 7 should be considered together as they represent various stages of the operation of the device and its features. Compared to FIG. 5 the body orientation is reversed in FIG. 6 to illustrate additional components more clearly.

In the preferred form of the invention the blade 15 is mounted to an elongate rail 30 which includes a blade rack 32 element. The rail 30 is a close fit with the body 16 so that the blade is held securely in the body when the blade is in the advanced position seen in FIG. 7.

The slider 14 reciprocates along the path 26 indicated by the arrow above the body. In FIG. 6 the slider 14 incorporates a slider rack element 36 which operates a small pinion gear 38 located on an axle 40. This axle 40 is journaled within the body 16 along axle axis 42 best seen in FIG. 2.

Linear motion imparted to the slider 14 is stepped up by the large pinion 48 which engages the blade rack 32. Motion of the blade 52 out of the body stretches spring 50. The overall gear ratios result in a 1:3 in the drawing of figures. The relationship between slider motion and blade motion although the direction is reversed in the sense that retrograde motion of the slider advances the blade. Other gear ratios are possible but ratios greater than between 1:1 are preferred with a ratio of and 1:3 preferred when used with a spring.

The cantilevered stop 56 feature engages a boss 58 formed in the body 16 to hold the blade holder 52 in the advanced and "locked" position against the retraction force of the spring 50. The detent mechanism formed by blade release 28, boss 58 and lever 56 cooperate to hold the blade open as best seen in FIG. 7 can be overcome by depressing the blade release 28 portion of the slider 14 which dislodges the cantilevered beam 56 from the boss 58. At this point the blade holder 52 and associated blade 15 are retracted under spring force and its motion may be controlled by the user's finger on the slider 14. Although a helical metal spring is shown in the figure for convenience it must be appreciated that an elastic band made of rubber of the like may readily substituted. In a similar fashion a "plastic" spring member made of the parent material is contemplated within the scope of the invention and are encompassed with the term spring member.

The comfort and utility of the tool depends in part on its' "feel". It is expected that adding weight to the tool will make it more acceptable to some physicians. The ballast 57 can be added to increase the weight of the tool. By placing the ballast off the center line of the tool the asymmetry of the design and the ballast cooperate to prevent the tool from rolling on an inclined surface. This is regarded as a desirable feature of the design.

What is claimed is:

1. A surgical tool comprising:

an elongate body;

a blade;

a blade rail carrying said blade and adapted for reciprocating motion in said body;

a gear rack on said blade rail;

an axle mounted for rotation in said body having a slider pinion and a blade rack pinion;

a slider rack on said slider;

whereby motion of the slider moves the blade in a ratio greater than one to one.

2. The surgical tool of claim 1 further comprising:

a detent formed by a lever feature on said blade rail, cooperating with a boss feature located in said body to hold said blade rail in a fully advanced position.

3. The surgical tool of claim 1 further comprising:

a spring member coupled between said blade rail and said body for retracting said blade rail and retaining said blade rail in a retracted position.

4. The surgical tool of claim 1 further comprising:

a rotable blade for rotation around the central axis of the body member.

5. The device of claim 1 wherein:

said housing is formed from a clear plastic material permitting observation of the blade in the retracted position.

6. The device of claim 1 wherein:

said body member is sufficiently asymmetrical in shape about the central axis that the body member will not roll on a horizontal surface.

7. The device of claim 6 further comprising:

a ballast weight located asymmetrically about the central axis of the body member such that said body member will not roll on a horizontal surface.

* * * * *